(12) United States Patent
Vonner et al.

(10) Patent No.: US 10,150,717 B2
(45) Date of Patent: Dec. 11, 2018

(54) PROCESS FOR THE SIMULATED MOVING BED SEPARATION OF XYLENES, AND OPTIMIZED OPERATING CONDITIONS

(71) Applicant: IFP Energies Nouvelles, Rueil-Malmaison (FR)

(72) Inventors: Alexandre Vonner, Feyzin (FR); Damien Leinekugel Le Cocq, Oullins (FR); Catherine Laroche, Vernaison (FR); Pascal Etienne, Estrablin (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/918,222

(22) Filed: Mar. 12, 2018

(65) Prior Publication Data

US 2018/0258013 A1  Sep. 13, 2018

(30) Foreign Application Priority Data

Mar. 13, 2017  (FR) .................................. 17 52007

(51) Int. Cl.
*C07C 7/13* (2006.01)
*B01D 15/18* (2006.01)

(52) U.S. Cl.
CPC ............ *C07C 7/13* (2013.01); *B01D 15/1828* (2013.01); *B01D 2215/023* (2013.01)

(58) Field of Classification Search
None
See application file for complete search history.

(56) References Cited

U.S. PATENT DOCUMENTS

| | | | |
|---|---|---|---|
| 5,470,482 A | 11/1995 | Holt | |
| 7,713,489 B2 * | 5/2010 | Wolff | B01D 15/1842 422/130 |
| 7,759,534 B2 | 7/2010 | Leflaive et al. | |
| 2009/0018380 A1 | 1/2009 | Leflaive et al. | |
| 2009/0326309 A1 * | 12/2009 | Priegnitz | B01J 20/183 585/820 |
| 2009/0326311 A1 * | 12/2009 | Cheng | B01J 20/183 585/828 |
| 2012/0330081 A1 * | 12/2012 | Cheng | B01D 15/185 585/824 |
| 2016/0009614 A1 * | 1/2016 | Laroche | B01D 15/1828 585/828 |

FOREIGN PATENT DOCUMENTS

WO  2009/019336 A1  2/2009

OTHER PUBLICATIONS

French Search Report dated Oct. 2, 2017 issued in corresponding FR 1752007 application (2 pages).

* cited by examiner

*Primary Examiner* — Tam M Nguyen
(74) *Attorney, Agent, or Firm* — Millen, White, Zelano and Branigan, P.C.

(57) ABSTRACT

The present invention describes a process for the simulated moving bed separation of xylenes, in which the operating conditions are optimized by means of a specific relationship between the cycle time and the flow rate of the desorbant.

5 Claims, No Drawings

PROCESS FOR THE SIMULATED MOVING BED SEPARATION OF XYLENES, AND OPTIMIZED OPERATING CONDITIONS

CONTEXT OF THE INVENTION

The present invention relates to the field of the separation of paraxylene from other aromatic C8 isomers. In order to carry out this separation, a family of processes and associated devices are used which are known by the name of simulated moving bed separation processes (abbreviated to SMB), or simulated counter-current separation, or in fact the VARICOL process, which we shall hereinafter designate by the general term of SCC separation processes (abbreviation for simulated counter-current). More precisely, the present invention is intended to optimize the operating conditions for a given unit by obtaining the cycle time as a function of the flow rate of desorbant with respect to the flow rate of paraxylene contained in the feed.

EXAMINATION OF THE PRIOR ART

SCC separation is well known in the prior art. As a general rule, a process for the separation of paraxylene operating in simulated counter-current mode comprises at least four zones, and optionally five or six, each of these zones being constituted by a certain number of successive beds, and each zone being defined by its position included between a supply point and a withdrawal point. Typically, a SCC unit for the production of paraxylene is supplied with at least one feed F to be fractionated (containing paraxylene and the other aromatic C8 isomers) and a desorbant D, sometimes known as the eluent (generally paradiethylbenzene or toluene), and at least one raffinate R containing the isomers of paraxylene and desorbant, and an extract E containing paraxylene and desorbant, are withdrawn from said unit.

The processes for the simulated moving bed separation of xylenes are conventionally operated with settings which are intended to maximize the productivity, at the expense of a high flow of desorbant, and thus high operating expenses (reboiling of distillations, pumps, etc).

The present invention concerns the field of low desorbant ratios, i.e. a low ratio between the flow rate of the desorbant and the flow rate of the feed, in which a compromise is found between the productivity and the reduction in the flow rate of the desorbant, and thus a reduction in the operating costs.

We have not found any prior art which specifically addresses the link between the flow rate of desorbant and the cycle time, i.e. the time during which the injections and withdrawals of the unit change along the column until they regain their original position.

BRIEF DESCRIPTION OF THE INVENTION

The present invention describes a unit for the simulated moving bed separation and purification of paraxylene contained in a feed of C8 isomers, the paraxylene content in the feed being in the range 18% to 25% by weight, and the ethylbenzene content being in the range 2% to 15% by weight. Compared with the prior art, this unit has an optimized setting. The term "optimized setting" means that the purity and yield performances as well as the maximum paraxylene productivity have been achieved for a given desorbant ratio. The simulated moving bed xylenes separation unit uses at least one column for which the number of beds is in the range 4 to 24, preferably in the range 6 to 18, and more preferably in the range 8 to 15.

The configuration of the unit may be defined by defining the mean number of beds for the zone j (j being in the range 1 to 4), Nzj, with respect to the total number of beds in the entire unit, N_total, as follows:

$$Nz1 = (N\_total * 5/24) * (1 \pm 0.2)$$

$$Nz2 = (N\_total * 9/24) * (1 \pm 0.2)$$

$$Nz3 = (N\_total * 7/24) * (1 \pm 0.2)$$

$$Nz4 = (N\_total * 3/24) * (1 \pm 0.2)$$

The four chromatographic zones are defined in the following manner:
zone 1: paraxylene desorption zone, included between the injection of desorbant D and the withdrawal of the extract E;
zone 2: desorption zone for paraxylene isomers, included between the withdrawal of the extract E and the injection of the feed to be fractionated F;
zone 3: paraxylene adsorption zone, included between the injection of the feed and the withdrawal of the raffinate R;
zone 4: zone located between the withdrawal of the raffinate R and the injection of the desorbant D.

The desorbant used in the context of the present invention is paradiethylbenzene.

The optimized settings for the simulated moving bed are described in the form of pairs of desorbant ratios for a weighted cycle time.

The desorbant ratio is the ratio of the flow rate of desorbant to the flow rate of paraxylene contained in the feed.

The cycle time is the interval of time separating two injections of desorbant at the same location in the adsorber. It is termed "weighted" here when it is multiplied by the factor:

$$\frac{\mu}{\sigma^2} \cdot \frac{1}{\varepsilon_i \cdot L_{lit}};$$

The ratio $$\frac{\mu}{\sigma^2},$$

expressed in $s^{-1}$, is determined by means of a breakthrough experiment as described in more detail in the detailed description of the invention below.

$L_{lit}$ represents the length of a bed, expressed in meters, and $\varepsilon_i$ represents the mean interstitial porosity of a bed of adsorbant.

The cycle time (interval of time separating two injections of desorbant at the same location in the column), which is optimized, is determined from the weighted cycle time using the following factor:

$$\text{weighted cycle time} = \text{cycle time} * \left[ \frac{\mu}{\sigma^2} \cdot \frac{1}{\varepsilon_i \cdot L_{lit}} \right]$$

the parameter $$\frac{\mu}{\sigma^2}$$

is in turn determined by means of a breakthrough experiment carried out on the one hand with the solid adsorbant, and on the other hand with a set of inert beads with 20 the same diameter as that of the solid adsorbant, in a manner such as to verify that the measurement of $\sigma^2$ obtained in the presence of adsorbant is at least 10 times higher, preferably 30 times higher than the measurement $\sigma^2_{blank}$ obtained during this same test carried out on the inert beads, knowing the length of a bed ($L_{bed}$) and its interstitial porosity ($\varepsilon_i$), the ratio of the flow rate of desorbant to the flow rate of paraxylene, and thus the optimal desorbant ratio, is determined using the following table:

|  | $t_{cycle}$, weighted (l/m) | $Q_D/Q_{PX}$ |
|---|---|---|
| Setting No. 1 | 320 +/− 20 | 6.7 +/− 0.3 |
| Setting No. 2 | 340 +/− 20 | 6.1 +/− 0.3 |
| Setting No. 3 | 360 +/− 20 | 5.7 +/− 0.3 |
| Setting No. 4 | 380 +/− 20 | 5.3 +/− 0.3 |
| Setting No. 5 | 405 +/− 20 | 5.1 +/− 0.3 |
| Setting No. 6 | 425 +/− 20 | 4.85 +/− 0.3 |
| Setting No. 7 | 452 +/− 20 | 4.6 +/− 0.3 |
| Setting No. 8 | 485 +/− 20 | 4.5 +/− 0.3 |

The operating conditions for the simulated moving bed xylenes separation process in accordance with the invention are as follows:

the operating temperature is generally in the range 100° C. to 250° C., preferably in the range 120° C. to 190° C., and more preferably in the range 165° C. to 185° C., the pressure is in the range between the bubble pressure of the mixture of xylenes constituting the feed and 3 MPa.

The water content in the feed for the simulated moving bed xylenes separation process in accordance with the claims for the invention is generally in the range 70 to 140 ppm, and preferably in the range 80 to 120 ppm.

The desorbant used in the xylenes separation process in accordance with the present invention is paradiethylbenzene.

DETAILED DESCRIPTION OF THE INVENTION

The problem that the present invention seeks to solve is that of setting, in an optimized manner, the simulated moving bed (SMB) process for the separation of xylenes in a low desorbant ratio range, in order to reduce the "run around" flow rate and to optimize the operating expenses (OPEX) of the process. The term "optimized setting" should be understood to mean a setting which can be used to obtain a minimum flow rate of desorbant for a given level of productivity, while guaranteeing the required levels of purity and yield: typically a paraxylene purity of more than 99.5%, preferably more than 99.6%, and more preferably more than 99.7%, and a paraxylene yield of more than 95%, preferably more than 96%, and more preferably more than 97%.

The prior art does not have a method for optimizing settings.

The invention concerns a process for the production of high purity paraxylene from a feed F comprising in the range 18% to 25% by weight of paraxylene, associated with its other aromatic C8 isomers.

In accordance with one characteristic of the process, the adsorbant for the process in accordance with the invention is a zeolitic adsorbant based on crystals of X zeolite and a non-zeolitic phase, preferably a faujasite type zeolite exchanged with barium or exchanged with barium and potassium.

SMB separation of paraxylene with a commercial purity, typically at least 99.7% by weight, is carried out industrially in SMB devices comprising n beds of adsorbant, n possibly being in the range 4 to 24, preferably in the range 6 to 18 beds, and more preferably in the range 8 to 15 beds. The number of beds is set in a manner such that each bed preferably has a height in the range 70 cm to 1.40 m.

The configuration of each zone, i.e. the mean number of beds per zone of the unit in accordance with the invention, may be with a fixed number of beds (the shifts for the various injection or withdrawal points thus being simultaneous), or variable. In the latter case, the shifts of the 2 injection points and the 2 withdrawal points are not simultaneous, in a manner such as to obtain numbers of beds per zone which is not a whole number on average during a cycle, as disclosed in the patent FR 2 785 196.

The configuration of the unit may be defined by defining the mean number of beds for the zone j (j being in the range 1 to 4), Nzj, with respect to the total number of beds in the whole of the unit, N_total, as follows. In these expressions, the first index z is the number of beds in the zone under consideration, and the second index j, which varies from 1 to 4, represents the zone under consideration.

$Nz1=(N\_total*5/24)*(1\pm0.2)$ $Nz2=(N\_total*9/24)*(1\pm0.2)$ $Nz3=(N\_total*7/24)*(1\pm0.2)$ $Nz4=(N\_total*3/24)*(1\pm0.2)$ By applying the above formulae, it is possible to arrive at non-integral numbers of beds. This 30 is not a problem in the context of the present invention, as there is a variation of the Eluxyl process, known as the "Varicol" process, which allows such an operation.

In general, the four chromatographic zones are defined as follows:

zone 1: paraxylene desorption zone, included between the injection of desorbant D and the withdrawal of the extract E;

zone 2: desorption zone for paraxylene isomers, included between the withdrawal of the extract E and the injection of the feed to be fractionated F;

zone 3: paraxylene adsorption zone, included between the injection of the feed and the withdrawal of the raffinate R;

zone 4: zone located between the withdrawal of the raffinate R and the injection of the desorbant D.

Advantageously, the cycle time, corresponding to the time between two injections of desorbant onto a given bed, is in the range 3 to 40 min, and preferably in the range 5 to 35 min.

Advantageously, the xylenes separation process is operated at a temperature of 175° C. ±10° C., and at a pressure in the range between the bubble pressure of the xylenes at the temperature of the process and 3 MPa.

Advantageously, the recycle ratio is in the range 2.0 to 8, preferably 2.5 to 5. The recycle ratio is defined as the ratio between the mean flow rate flowing in the various beds of the adsorber and the flow rate for injection of the feed into that adsorber.

The water content in the liquid phase is maintained at a content in the range 80 to 120 ppm (by weight).

In the paraxylene separation process in accordance with the invention, the desorbant is paradiethylbenzene.

In addition to the high adsorption capacity and the good selectivity properties as regards the species to be separated from the reaction mixture, the adsorbant has to have good material transfer properties in order to guarantee a sufficient number of theoretical plates to carry out an effective separation of the species in the mixture, as indicated by Ruthven in the publication entitled "Principles of Adsorption and Adsorption Processes", John Wiley & Sons, (1984), pages 326 and 407.

In order to estimate the overall material transfer of a bed of adsorbant, a simple technique consists of carrying out a chromatographic experiment, in which the adsorbant packed in a column is subjected to a perturbation of the concentration at the column inlet. This technique is described in the following document:

Silva, M. S. P.; Moreira, M. A.; Ferreira, A. F. P.; Santos, J. C.; Silva, V. M. T. M.; Sá Gomes, P.; Mineva, M.; Mota, J. P. B.; Rodrigues, A. E. "Adsorbant Evaluation Based on Experimental Breakthrough Curves: Separation of p-Xylene from C8 Isomers". Chem. Eng. Technol. 2012, 35, 1777-1785.

The analysis of the concentration front at the outlet from the column as a function of time, denoted c(t), in response to the perturbation in concentration at the inlet can be used to estimate the adsorption and overall material transfer properties.

When the perturbation at the inlet is a scale of concentration, the experiment which is carried out is known as a "breakthrough" experiment and the concentration front obtained at the outlet from the column as a function of time is known as the "breakthrough curve".

In the publication entitled "Diffusion in Nanopores", by Kärger, Ruthven and Theodorou, ed. Wiley (2012), the analysis of the experimental response of a chromatographic column using the method of moments is described in Chapter 14, pages 464-465.

In the case of a breakthrough in response to a scale of concentration $c_0$, the first and second moments of the concentration front c(t) at the outlet from the column as a function of time are given by the following expressions:

$\mu$, the first moment of the breakthrough curve, i.e. the mean time $\bar{t}$ for the concentration front to leave the chromatographic column:

$$\mu = \bar{t} = \int_0^\infty \left(1 - \frac{c}{c_0}\right) dt$$

$\sigma^2$, the centred second moment of the breakthrough curve, which translates as the dispersion of the concentration front:

$$\sigma^2 = 2\int_0^\infty \left(1 - \frac{c}{c_0}\right) t\, dt - \mu^2$$

c(t) is the concentration function as a function of time following the perturbation $c_0$ introduced at the inlet.

It is important to ensure that the measurement of $\sigma^2$ is representative of the overall material transfer in the adsorbant and not only of the dispersion linked to the hydrodynamics in the column and in the lines of the test tool. To accomplish this, a breakthrough test must be carried out under the same conditions as the test carried out with a column filled with adsorbant, but filling the column with glass beads with a diameter comparable with the diameter of the adsorbant. The measurement of $\sigma^2$ obtained in the presence of adsorbant must be at least 10 times higher, preferably 30 times higher than the measurement $\sigma^2_{blank}$ obtained during this test in the absence of adsorbant.

The cycle time is one of the operating parameters, like the flow rates for the injection of feed, desorbant, and the flow rates for withdrawal of the extract and the raffinate, which are defined by the operators of the process on a case by case basis. There is no systematic method for setting in the current prior art.

The present invention describes the relationship between:

the desorbant ratio, expressed as the ratio of the flow rate of desorbant $Q_D$ to the flow rate of paraxylene in the feed, $Q_{PX}$, $t_{cycle}$, the minimum cycle time for the process, weighted by the ratio of the first moment for breakthrough, $\mu$, to the product of the centred second moment for breakthrough, $\sigma^2$, $L_{bed}$, the length of the bed, and $\varepsilon_i$, the porosity of the pile of solid adsorbant:

$$t_{cycle, weighted} = t_{cycle} \cdot \frac{\mu}{\sigma^2} \cdot \frac{1}{\varepsilon_i \cdot L_{bed}}$$

The weighted cycle time is thus linked to the cycle time by a group of parameters which are the first and second moments of the breakthrough curve obtained experimentally, and two parameters which are representative of the bed: its length ($L_{bed}$) and its interstitial porosity ($\varepsilon_i$). The unit for this weighted cycle time is thus the inverse of a length, and thus expressed as $m^{-1}$.

The invention thus described is applicable irrespective of the solid adsorbant material transfer properties and the configuration of the process which are accounted for by the weighting factor for the cycle time.

The first and second breakthrough moments are determined for a given superficial velocity of the mixture injected during the breakthrough experiment, equal to 1.30 cm/s±0.05 cm/s under the temperature conditions of the test, i.e. 175° C., and for a given length of the column in which the solid adsorbant is packed, equal to 1.00 m±0.01 m.

The optimized settings described by the invention are presented in the table below:

|  | $t_{cycle}$, weighted (1/m) | $Q_D/Q_{PX}$ |
|---|---|---|
| Setting No. 1 | 320 +/− 20 | 6.7 +/− 0.3 |
| Setting No. 2 | 340 +/− 20 | 6.1 +/− 0.3 |
| Setting No. 3 | 360 +/− 20 | 5.7 +/− 0.3 |
| Setting No. 4 | 380 +/− 20 | 5.3 +/− 0.3 |
| Setting No. 5 | 405 +/− 20 | 5.1 +/− 0.3 |
| Setting No. 6 | 425 +/− 20 | 4.85 +/− 0.3 |
| Setting No. 7 | 452 +/− 20 | 4.6 +/− 0.3 |
| Setting No. 8 | 485 +/− 20 | 4.5 +/− 0.3 |

These points describe the optimal settings for which the paraxylene productivity is a maximum for the desorbant ratio under consideration.

The settings with a lower desorbant ratio or with a smaller weighted cycle time cannot hit the targets regarding purity and yield for the process.

The settings with a higher desorbant ratio or with a higher weighted cycle time can produce the performances, but either the paraxylene productivity is lower than its optimal value, or the desorbant ratio is not as low as possible for this productivity. Thus, the intention is to get as close as possible to these settings of interest.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1752007, filed Mar. 13, 2017 are incorporated by reference herein.

EXAMPLES IN ACCORDANCE WITH THE INVENTION

The invention will be better understood from the following three examples: the first corresponds to a unit set in an optimized manner in accordance with the invention; the second corresponds to an "under-performing" unit set to the same desorbant ratio; and the third corresponds to an "over-performing" unit set to the same desorbant ratio.

A breakthrough test (frontal chromatography) was carried out on the adsorbants with the aim of evaluating the reduced second moment $$\frac{\sigma^2}{2\mu^2}$$

as a function of the superficial velocity of the injected fluid. The breakthrough consisted of continuously injecting the feed containing one or more of the compounds which were to be adsorbed through a column filled with adsorbant. The column had been saturated with a solvent. The column used was 1.00 meter in length and had an internal diameter of 0.77 cm; and the quantity of solid adsorbant for this test was approximately 40 g.

The mode of operation for obtaining the breakthrough curves was as follows:
  Filling the column with solid adsorbant and positioning in the test bench.
  Filling with solvent at ambient temperature.
  Slowly raising the adsorption temperature in a stream of solvent (flow rate at ambient temperature set at 5 cm$^3$/min).
  Injecting solvent at 30 cm$^3$/min (flow rate set at ambient temperature) when the adsorption temperature is reached.
  Solvent/feed switching in order to inject the feed (flow rate at ambient temperature set at 30 cm$^3$/min).
  Continuously and incrementally collecting breakthrough effluent in closed vials, and analysis of the effluent collected in the vials by gas phase chromatography.
  Maintaining injection of the feed for a time sufficient to reach thermodynamic equilibrium, i.e. until the concentration of solvent in the effluent is zero.

The solvent used was orthoxylene. The feed used was solely constituted by metaxylene.

The test was carried out with an adsorption temperature of 175° C. The pressure was sufficient for the feed to remain in the liquid phase, i.e. 1 MPa.

Two tests were carried out: one test with the column filled with glass beads with a granulometry of 400-600 μm from which the $\sigma^2$, blank was evaluated, and a second test with the same column (or an identical column) filled with adsorbant with a granulometry of 400-600 μm, from which the first, μ, and the centred second moment, $\sigma^2$, were evaluated.

The results are shown in the table below:

| | | |
|---|---|---|
| Superficial velocity, liquid | 1.30 | cm/s |
| $\sigma^2_{blank}$ | 0.001 | min$^2$ |
| 1$^{st}$ moment μ | 0.98 | min |
| $\sigma^2$ | 0.129 | min$^2$ |
| $\sigma^2/\sigma^2_{blank}$ | 129 | |
| $\sigma^2/2 \cdot \mu^2$ | 0.067 | |
| $\mu/\sigma^2$ | 7.69 | 1/min |

Determination of Second Moment from a Breakthrough Experiment

Example 1

Optimally Set Unit

A simulated moving bed unit constituted by 15 beds, each with a length of 1.24 m, with an interstitial porosity of 39.6% and with an internal radius of 1.05 m was considered, having an injection of feed, an injection of desorbant, a withdrawal of extract and a withdrawal of raffinate.

The adsorbant considered was a zeolitic BaX type solid characterized by breakthrough using the method described above, with a ratio $\mu/\sigma^2=7.69$ 1/min.

The desorbant was paradiethylbenzene. The temperature was 175° C.; the pressure was 15 bar. The water content was 95 ppm (by weight).

The feed to be separated was composed of 20% of paraxylene, 27.3% of orthoxylene, 47.7% 20 of metaxylene and 5% of ethylbenzene.

The shifts for the various injection or withdrawal points were simultaneous. The beds were divided into 4 chromatographic zones in accordance with the configuration 3/6/4/2.

The flow rates for the injection of feed and desorbant were as follows:
  0.586 m$^3$·min$^{-1}$ for the feed,
  0.577 m$^3$·min$^{-1}$ for the desorbant.
In addition, the flow rate for zone 4 was 1.522 m$^3$·min$^{-1}$, and the flow rate for withdrawal of the extract was 0.286 m$^3$·min$^{-1}$. The weighted cycle time was 396.1 m$^{-1}$.

By simulation, a purity of 99.78% for the paraxylene purity and a paraxylene yield of 97.7% with a productivity of 87.2 kgp$_{PX}$·h$^{-}$/m$^{-3}$ were obtained.

This level of performance in terms of purity and paraxylene yield was in accordance with the targets for the process, and was used as a reference for the next examples.

Example 2

"Under-Performing" Unit

Starting from the unit considered to have been set in an optimal manner in terms of paraxylene purity and yield, presented in Example 1, the cycle time was to be reduced in order to improve the productivity, while retaining the same desorbant ratio.

Again, a simulated moving bed unit constituted by 15 beds, each with a length of 1.24 m, with an interstitial porosity of 39.6% and with an internal radius of 1.05 m was considered, having an injection of feed, an injection of desorbant, a withdrawal of extract and a withdrawal of raffinate.

The adsorbant considered was a zeolitic BaX type solid characterized by breakthrough using the method described above, with a ratio $\mu/\sigma^2 = 7.69$ 1/min.

The desorbant was paradiethylbenzene. The temperature was 175° C.; the pressure was 15 bar.

The water content was 95 ppm (by weight).

The feed was composed of 20% of paraxylene, 27.3% of orthoxylene, 47.7% of metaxylene and 5% of ethylbenzene.

The shifts for the various injection or withdrawal points were simultaneous. The beds were divided into 4 chromatographic zones in accordance with the configuration 3/6/4/2.

The flow rates for the injection of feed and desorbant were as follows:

0.623 m$^3$·min$^{-1}$ for the feed,
0.613 m$^3$·min$^{-1}$ for the desorbant.

In addition, the flow rate for zone 4 was 1.618 m$^3$·min$^{-1}$, and the flow rate for withdrawal of the extract was 0.304 m$^3$·min$^{-1}$. The weighted cycle time was 372.6 m$^{-1}$.

By simulation, a purity of 99.65% for the paraxylene purity and a paraxylene yield of 97.1% with a productivity of 92.2 kg$_{PX}$·h$^{-1}$·m$^{-3}$ were obtained. Thus, the unit set in this manner was "under-performing" compared with the purity and yield targets, which were respectively 99.78% and 97.7%.

Example 3

"Over-Performing" Unit

Starting from the unit considered in Example 1, the cycle time was to be increased in order to improve the performances in terms of purity and paraxylene yield, while retaining the same desorbant ratio.

Again, a simulated moving bed unit constituted by 15 beds, each with a length of 1.24 m, with an interstitial porosity of 39.6% and with an internal radius of 1.05 m was considered, having an injection of feed, an injection of desorbant, a withdrawal of extract and a withdrawal of raffinate.

The adsorbant considered was a zeolitic BaX type solid characterized by breakthrough using e method described above, with a ratio $\mu/\sigma^2 = 7.69$ 1/min.

The desorbant was paradiethylbenzene. The temperature was 175° C.; the pressure was 15 bar. 20 The water content was 95 ppm (by weight).

The feed was composed of 20% of paraxylene, 27.3% of orthoxylene, 47.7% of metaxylene and 5% of ethylbenzene.

The shifts for the various injection or withdrawal points were simultaneous. The beds were divided into 4 chromatographic zones in accordance with the configuration 3/6/4/2.

The flow rates for the injection of feed and desorbant were as follows:

0.553 m$^3$·min$^{-1}$ for the feed,
0.544 m$^3$·min$^{-1}$ for the desorbant.

In addition, the flow rate for zone 4 was 1.437 m$^3$·min$^{-1}$, and the flow rate for withdrawal of the extract was 0.270 m$^3$·min$^{-1}$. The weighted cycle time was 419.6 m$^{-1}$.

By simulation, a purity of 99.85% for the paraxylene purity and a paraxylene yield of 98.1% with a productivity of 82.7 kg$_{PX}$·h$^{-1}$·m$^{-3}$ were obtained. The unit set in this manner was "over-performing" compared with the purity and yield targets, which were respectively 99.78% and 97.7%.

These examples provide a good illustration of setting up the process in accordance with the invention in order to determine the cycle time which can be used to obtain optimal performances for a given desorbant ratio, namely simultaneously, the target levels for purity and paraxylene yield, as well as the maximum productivity for these settings.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the simulated moving bed separation of xylenes with the aim of optimizing the purity and paraxylene yield, the content of paraxylene in the feed being in the range 20% to 25% by weight, said unit using a number of beds in the range 4 to 24, and the distribution of the beds in the various zones being given by the general formula which is applicable irrespective of the total number of beds, N_total:

$$Nz1 = (N\_total * 5/24) * (1 \pm 0.2)$$

$$Nz2 = (N\_total * 9/24) * (1 \pm 0.2)$$

$$Nz3 = (N\_total * 7/24) * (1 \pm 0.2)$$

$$Nz4 = (N\_total * 3/24) * (1 \pm 0.2)$$

the four chromatographic zones being defined in the following manner:
- zone 1: paraxylene desorption zone, included between the injection of desorbant D and the withdrawal of the extract E;
- zone 2: desorption zone for paraxylene isomers, included between the withdrawal of the extract E and the injection of the feed to be fractionated F;
- zone 3: paraxylene adsorption zone, included between the injection of the feed and the withdrawal of the raffinate R;
- zone 4: zone located between the withdrawal of the raffinate R and the injection of the desorbant D,
- the optimized cycle time, defined as the interval of time separating two injections of desorbant at the same location in the column, being determined from the weighted cycle time using the following correction factor:

$$\text{weighted cycle time} = \text{cycle time} * \left[ \frac{\mu}{\sigma^2} \cdot \frac{1}{\varepsilon_i \cdot L_{bed}} \right]$$

the parameter $$\frac{\mu}{\sigma^2}$$

in turn being determined by means of a breakthrough experiment carried out on the one hand with the solid adsorbant, and on the other hand with a set of inert beads with the same diameter as that of the solid adsorbant, in a manner such as to verify that the measurement of $\sigma^2$ obtained in the presence of adsorbant is at least 10 times higher than the measurement $\sigma^2_{blank}$ obtained during this same test carried out on the inert beads, knowing the length of a bed ($L_{bed}$) and its interstitital porosity ($\varepsilon_i$), the ratio of the flow rate of desorbant to the flow rate of paraxylene, and thus the optimal desorbant ratio, is determined using the following table:

|  | t_cycle, weighted (l/m) | $Q_D/Q_{PX}$ |
|---|---|---|
| Setting No. 1 | 320 +/− 20 | 6.7 +/− 0.3 |
| Setting No. 2 | 340 +/− 20 | 6.1 +/− 0.3 |
| Setting No. 3 | 360 +/− 20 | 5.7 +/− 0.3 |
| Setting No. 4 | 380 +/− 20 | 5.3 +/− 0.3 |
| Setting No. 5 | 405 +/− 20 | 5.1 +/− 0.3 |
| Setting No. 6 | 425 +/− 20 | 4.85 +/− 0.3 |
| Setting No. 7 | 452 +/− 20 | 4.6 +/− 0.3 |
| Setting No. 8 | 485 +/− 20 | 4.5 +/− 0.3. |

2. The simulated moving bed xylenes separation process as claimed in claim 1, in which the operating temperature is in the range 100° C. to 250° C., and the pressure is in the range between the bubble pressure of the mixture of xylenes constituting the feed and 3 MPa.

3. The simulated moving bed xylenes separation process as claimed in claim 1, in which the water content in the feed is in the range 70 to 140 ppm.

4. The simulated moving bed xylenes separation process as claimed in claim 1, in which the desorbant is paradiethylbenzene.

5. The simulated moving bed xylenes separation process as claimed in claim 1, in which the recycle ratio is in the range 2.0 to 8, the recycle ratio being defined as the ratio between the mean flow rate flowing in the various beds of the adsorber and the flow rate for injection of feed into said adsorber.

* * * * *